United States Patent [19]

Jacobi et al.

[11] 4,349,543
[45] Sep. 14, 1982

[54] HISTOLYTIC AGENTS AND THEIR USE

[75] Inventors: Haireddin Jacobi, Leichlingen; Wolfgang Opitz; Eugen Etschenberg, both of Cologne, all of Fed. Rep. of Germany

[73] Assignee: Troponwerke GmbH & Co. KG, Cologne, Fed. Rep. of Germany

[21] Appl. No.: 108,315

[22] Filed: Dec. 31, 1979

[30] Foreign Application Priority Data

Jan. 17, 1979 [DE] Fed. Rep. of Germany ....... 2901667

[51] Int. Cl.$^3$ .................. A61K 37/02; A61K 37/00
[52] U.S. Cl. .......................... 424/177; 260/112.5 R
[58] Field of Search ................. 424/177, 45; 260/112.5 R

[56] References Cited

U.S. PATENT DOCUMENTS 3,965,260  6/1976  McArthur et al. ............... 424/177

OTHER PUBLICATIONS

Wilchek, M. et al., J. Organic Chemistry, vol. 28, 1874.

*Primary Examiner*—Blondel Hazel

[57] ABSTRACT

The invention relates to pharmaceutical compositions containing as an active ingredient a dipeptide or an acid salt or a base addition salt thereof or a stereoisomer thereof, said dipeptide being those of the formula

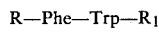

in which
Phe denote the radical

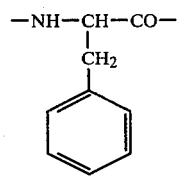

Trp denotes the radical

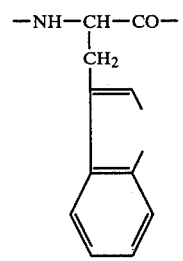

R denotes a hydrogen atom or a $C_1$ to $C_6$ optionally substituted alkanoyl group and
$R_1$ denotes a hydroxyl, $C_1$ to $C_4$ alkoxy, amino, $C_1$ to $C_4$ alkylamino or di-$C_1$ to $C_4$ alkylamino group.

3 Claims, No Drawings

HISTOLYTIC AGENTS AND THEIR USE

The present invention relates to the use as histolytic agents of certain dipeptide compounds, some of which are known. (Mc Arthur, U.S. Pat. No. 3,965,260)

It is already known that histolytic effect can be achieved with substances of the most diverse nature. However, in most cases the general toxicity of such compounds is so high that possibilities for treatment which can easily be manipulated therapeutically and which do not harm the patient even further do not exist.

It has therefore been proposed to employ dehydrooligopeptides (DT-OS (German Published Specification) 2,569,154), which have a low toxicity but, compared with the compounds according to the invention, have some disadvantages.

According to the present invention there are provided pharmaceutical composition containing as an active ingredient a dipeptide of the following formula, R—Phe—Trp—R₁ (I)

an acid salt or a base addition salt thereof or a stereoisomer thereof, in which
Phe denote the radical

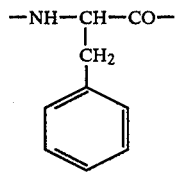

Trp denotes the radical

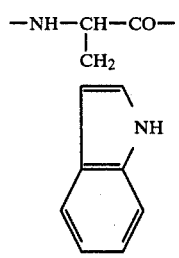

R denotes a hydrogen atom or a $C_1$ to $C_6$ optionally substituted alkanoyl group and
$R_1$ denotes a hydroxyl, $C_1$ to $C_4$ alkoxy, amino, $C_1$ to $C_4$ alkylamino or di-$C_1$ to $C_4$ alkylamino group, an admixture with a solid or liquefied gaseous diluent or in admixture with a liquid diluent other than a solvent of a molecular weight less than 200 except in the presence of a surface-active agent. The pharmaceutical compositions of the present invention have histolytic effects.

The present invention also comprises the following, hitherto unknown compound: H—D—Phw—D—Trp—NH₂, H—D—Phe—D—Trp—OMe, Ac—D—Phe—D—Trp—OH and Ac—D—Phe—D—Trp—NH₂ and their salts.

In addition to the above-mentioned symbols, the following abbreviations have the meanings given below throughout the text:

| | |
|---|---|
| Ac = acetyl | (CH₃CO—) |
| Me = methyl | (CH₃—) |
| Boc = tert.-butoxycarbonyl | 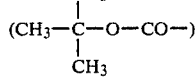 |

In the formula I, the $C_1$ to $C_6$ optionally substituted alkanoyl group R is a saturated straight-chain or branched alkanoyl group, preferably a formyl, acetyl, propionyl, acryl, crotonyl, butyryl or valeryl group, and the acetyl group is particularly preferred. These groups are preferably optionally substituted by a hydroxyl group or by one or more halogen atoms, preferably chlorine, bromine or fluorine atoms.

The alkoxy, alkylamino and dialkylamino groups $R_1$ contain methyl, ethyl, propyl, isopropyl or the various straight-chain or branched butyl groups and those which contain the methyl group are particularly preferred.

Particularly preferred pharmaceutical compositions are thos in which R denotes a hydrogen atom or an acetyl group and $R_1$ denotes a hydroxyl, amino, alkoxy with 1 or 2 carbon atoms or alkylamino or dialkylamino with in each case 1 or 2 carbon atoms in the alkyl groups, also those in which R denotes a hydrogen atom and $R_1$ denotes a hydroxyl group.

The compounds according to the invention are prepared in a manner which is in itself known, by the usual methods customary in peptide chemistry (compare Houben-Weyl, Methoden der organischen Chemie (Methods of Organic Chemistry), Volumes 15/1 and 15/2).

The following reaction course may be mentioned by way of example:

With the amino group protected by the tert.-butoxycarbonyl group, phenylalanine, as Boc-Phe-OH, is subjected to a condensation reaction with the methyl ester of tryptophane, Trp—OMe. HCl, at a low temperature in the presence of an acid-binding agent and a condensing agent, for example dicyclohexylcarbodiimide, to give Boc—Phe—Trp—OMe, the ester grouping is then first saponified with an alkali to give Boc—Phe—Trp—OH, and finally the tert.butoxycarbonyl group is split off with an acid (H—Phe—Trp—OH).

If one of the two aminoacide is present in the D, L-form, the diastereometer pairs can be separated by chromatography on silica gel, on the basis of their different physical properties.

In the case where R in the general formula I is an alkanoyl group, the free amino group of the corresponding dipeptide ester is acylated in a known manner (Helv. Chim. Acta 41 (1958), 1852).

In the case where $R_1$ is an amino group, the particular methyl ester is converted into the amide in the customary manner by reaction with NH₃.

Examples of the active compounds according to the invention which may be mentioned are: H—Phe—Trp—OH, H—Phe—D—Trp—PH, H—D—Phe—Trp—OH, H—D—Phe—D—Trp—OH, H—D—Phe—D—Trp—OMe, Ac—D—Phe—D—Trp—OMe—, Ac—D—Phe—D—Trp—OH, Ac—D—Phe—D—Trp—NH₂ and H—D—Phe—Trp—NH₂.

The active compounds according to the invention have other histolytic action which depends on the dose, and are preferably applied locally.

By local administration these are to be understood herein as being included in particular, the following types of administration: subcutaneous or administration. Necroses usually occur in the intermediate region of the point of administration. If the necrotic region breaks open, it is free from putrid material even for a relatively long period although in the case of the experimental animals feed, faeces, sawdust and other material came into contact with the open wound.

The necrotic tissue is sharply divided from the surrounding healthy tissue; it appears macroscopically and microscopically as if it were "stamped out".

The general behaviour of the experimental animals is not influenced by the size of the necrosis. There is no poisoning of the entire organism.

In the acute test for intravenous injection in rats, the $LD_{50}$ of the compounds according to the invention is greater than 200 mg/kg.

The present invention also includes the use of the active compounds according to the invention, as well as of pharmaceutical formulations which contain one or more active compounds according to the invention, for the treatment of those tissues in the field of medicine which prevent and interfere with the course of the normal biological function.

In addition, the compounds according to the invention can be used for fibrotic tissues of every type, in particular for the treatment of keloids, Ulcera crura, burn ulcers, decubital ulcers as well as Clavi and onychomycoses and scar tissue and for the therapy and prophylaxis of emboli and thromboses.

The compounds according to the invention can also be used for resolving moles, warts, atheromas and lipomas and for removing deep abscesses which, under certain circumstances, are fistulas.

The compounds according to the invention can additionally be used for the regeneration of cavernomas and tuberculomas.

The compounds according to the invention can also be used for the scar-free regeneration of tissue defects in the case of leprosy and other skin, mucous membrane and epithelium defects of various origins, above all those which are caused by infections by bacteria, fungi and pathogens of tropical diseases, for example, those of leishmanioses, framboesia and pinta.

As stated above, the invention also relates to the use in medicine of the compounds of the invention.

The present invention provides a pharmaceutical composition containing as active ingredient a compound of the invention in admixture with a solid or liquefied gaseous diluent, or in admixture with a liquid diluent other than a solvent of a molecular weight less than 200 (preferably less than 350) except in the presence of a surface active agent.

The invention further provides a pharmaceutical composition containing as active ingredient a compound of the invention in the form of a sterile and/or physiologically isotonic aqueous solution.

The invention also provides a medicament in dosage unit form comprising a compound of the invention.

The invention also provides a medicament in the form of ampoules or suppositories comprising a compound of the invention.

"Medicament" as used in this Specification means physically discrete coherent portions suitable for medical administration. "Medicament in dosage unit form" as used in this Specification means physically discrete coherent untis suitable for medical administration each containing a daily dose or a multiple (up to four times) os submultiple (down to a fortieth) of a daily dose of the compound of the invention in association with a carrier and/or enclosed within an envelope. Whether the medicament contains a daily dose or, for example, a half, a third or a quarter of a daily dose will depend on whether the medicament is to be administered once or, for example, twice, three times or four times a day respectively.

The pharmaceutical compositions according to the invention may, for example, take the form of ointments, gels, pastes, creams, sprays (including aerosols), lotions, suspensions, solutions and emulsions of the active ingredient in aqueous or non-aqueous diluents or powders.

The pharmaceutical compositions which are ointments, pastes, creams and gels can, for example, contain the usual diluents, e.g. animal and vegetable fats, waxes, paraffins, starch, tragacanth, cellulose derivatives, polyethylene glycols, silicones, bentonites, silicic acid, talc and zinc oxide or mixtures of these substances.

The pharmaceutical compositions which are powders and sprays can, for example, contain the usual diluents, e.g. lactose, talc, silicic acid, aluminium hydroxide, calcium silicate, and polyamide powder or mixtures of these substances. Aerosol sprays can, for example, contain the usual propellants, e.g. chlorofluorohydrocarbons.

The pharmaceutical compositions which are solutions and emulsions ca, for example, contain the customary diluents (with, of course, the above-mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils (for example ground nut oil), glycerol, tetrahydrofurfuryl alcohol, polyethylene glycols and fatty acid esters of sorbitol or mixtures thereof.

For parenteral administration, solutions and emulsions should be sterile, and, if appropriate, blood-isotonic.

Preferred injection solutions are those having a pH of from 7 to 9.5 most preferably from 8 to 9. The compounds of the invention which are free acids may be conveniently dissolved in dilute physiologically acceptable bases, then brought to the required pH by the addition of a dilute physiologically acceptable acid. Example of physiologically acceptable bases are inorganic hydroxides, carbonates and bicarbonates, particularly those of sodium and potassium. Examples of physiologically acceptable acids which may be mentioned are organic acids, such as citric acid, oxalic acid, lactic acid, benzoic acid, salicyclic acid or acetic acid, or also inorganic acids, such as, for example, dilute hydrochloric or sulphuric acids.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbits and sorbitane esters), microcrystalline cellulose, aluminum metahydroxide, bentonite, agar-agar and tragacanth or mixtures thereof.

All the pharmaceutical compositions according to the invention can also contain colouring agents and preservatives as well as perfumes.

The pharmaceutical compositions according to the invention generally contain from 1 to 90%, usually from 5 to 50% of the active ingredient by weight of the total composition.

In addition to a compound of the invention, the pharmaceutical compositions and medicaments according to the invention can also contain other pharmaceutically active compounds. They may also contain a plurality of compounds of the invention.

Any diluent in the medicaments of the present invention may be any of those mentioned above in relation to the pharmaceutical compositions of the present invention. Such medicaments may include solvents of molecular weight less than 200 as sole diluent.

The discrete coherent portions constituting the medicament according to the invention will generally be adapted by virtue of their shape or packaging for medical administration and may be, for example, suppositories and ampoules.

The preferred daily dose for administration of the medicaments of the invention is 50 to 2,500 mg of active ingredient.

The production of the above-mentioned pharmaceutical compositions and medicaments is carried out by any method known in the art.

This invention further provides a method of combating the above-mentioned diseases in warm-blooded animals, which comprises administering to the animals a compound of the invention alone or in admixture with a diluent or in the form of a medicament according to the invention.

It is envisaged that these active compounds will be administered at the site of the disease parenterally (for example intracutaneously or subcutaneously), or locally, preferably locally. Preferred pharmaceutical compositions and medicaments are therefore those adapted for administration such as local administration. Administration in the method of the invention is preferably local administration.

In general it has proved advantageous to the administer amounts of from 0.1 mg to 100 mg/kg, preferably 1 mg to 50 mg/kg, of body weight per day to achieve effective results. Nevertheless, it can at times be necessary to deviate from those dosage rates, and in particular to do so as a function of the nature and body weight of the animal subject to be treated, the individual reaction of this subject to the treatment, the type of formulation in which the active ingredient is administered and the mode in which the administration is carried out, and the point in the progress of the disease or interval at which it is administered. Thus it may in some case suffice to use less than the above-mentioned minimum dosage rate, whilst other cases the upper limit mentioned must be exceeded to achieve the desired results. Where larger amounts are administered it can be advisable to divide these into several individual administrations over the course of the day.

The following Examples illustrate the production of compounds for use in the pharmaceutical compositions of the present invention, including the production of those compounds which are novel.

EXAMPLE 1 (H—Phe—Trp—OH and H—Phe—D—Trp—OH)

(a) Boc—Phe—D, L—Trp—OMe 5.6 g (40 mmols) of N-ethylmorpholine, 13 g (49 mmols) of Boc—Phe—OH in 40 ml of methylene chloride and 10.1 g (49 mmols) of dicyclohexylcarbodiimide are added to a suspension of 12.5 g (49 mmols) of H—D, L—Trp—OMe. HCl in 60 ml of methylene chloride at 0° C., whilst stirring. After stirring the mixture at 0° C. for 2 hours, the precipitate which has separated out is filtered off and washed with methylene chloride and the filtrate is diluted with 300 ml of ethyl acetate. After extracting the solution by washing several times with saturated $KHCO_3$ solution, NaCl solution and 10% strength citric acid, the product phase is dried over $Na_2SO_4$ and evaporated in vacuo. 22.8 g of an oily crude product comprising Boc—Phe—D, L—Trp—OMe are obtained, and the product is not purified since a mixture of diastereoisomers with different physical properties is present.

This also applies to other examples.

(b) Boc—Phe—D, L—Trp—OH 36.8 ml of 2 N NaOH are added dropwise to a solution of the above crude product in 80 ml of tetrahydrofurane and 8 ml of water at 0° C. whilst stirring, and the mixture is stirred at room temperature for 1½ hours. The batch is then diluted with 600 ml of water and extracted several times with ethyl acetate. The aqueous phase is then adjusted to pH 2 with citric acid and extracted three times with ethyl acetate and the extract is dried over $Na_2SO_4$ and evaporated in vacuo. 19.3 g (87.5% of theory) of Boc—Phe—D, L—Trp—OH are obtained as a crude product.

(c) H—Phe—Trp—OH and H—Phe—D—Trp—OH

A solution of 9.6 g (21.3 mmols) of the above crude product in 60 ml of 80% strength formic acid is kept under nitrogen at room temperature for 6 hours and at 35° C. for 45 minutes and is then diluted with 100 ml of water and extracted with ether. The organic phase is extracted with water and the combined aqueous phases are lyophilised. The resulting crude isomer mixture is then chromatographed, in gram portions, from isopropanol/water (5:1) on 2 silica gel 60 pre-packed columns size C (Merck, Darmstadt) connected in series. After recrystallisation of the products from methanol/water, 1.7 g of H—Phe—Trp—OH (22.7% of theory), melting point 263°-266° C., 1,7 g (22.7% of theory) of H—Phe—D—Trp—OH, melting point 155° C., $(a)_D^{20} = +30.7°$ (c=1; methanol) and a mixed fraction of 2.6 g (34.6% of theory) are thus obtained. The yields are related to the diastereomer pair is 100%.

EXAMPLE 2 (H—D—Phe—Trp—OH)

(a) Boc—D, L—Phe—Trp—OMe 12.6 g (49.5 mmols) of H—Trp—OMe. HCl are dissolved in 80 ml of dimethylformamide, and 7 ml of triethylamine and 22 g (49.5 mmols) of Boc—D, L—Phe—OTcp are added at 0° C., whilst stirring. After standing for 2½ hours, the reaction mixture is diluted with 700 ml of water and extracted 3 times with ethyl acetate. The extract is washed with saturated $KHCO_3$ solution and then with 10% strength citric acid and with saturated NaCl solution and is dried over $Na_2SO_4$ and evaporated in vacuo. After the evaporation in vacuo, 23 g of Boc—D, L—Phe—Trp—OMe are obtained as a crude product.

(b) Boc—D, L—Phe—Trp—OH

The crude product described above under (a) is dissolved in 150 ml of tetrahydrofurane and 15 ml of water, 55 ml of 2 N NaOH solution are added dropwise at 0° to 5° C., whilst stirring, and the mixture is then stirred at room temperature for 1 hour, diluted with 1.3 l of water and extracted twice with ethyl acetate. The aqueous phase is adjusted to pH 2 with concentrated citric acid solution and is extracted 3× with ethyl acetate and the extracts are washed with saturated NaCl solution until neutral, dried over Na₂SO₄ and evaporated in vacuo. 22.4 g of Boc—D, L—Phe—Trp—OH are obtained as an oily crude product.

(c) H—Phe—Trp—OH and H—D—Phe—Trp—OH

The crude product obtained above under (b) is dissolved in 70 ml of 80% strength formic acid and the solution is kept at room temperature for 5½ hours and in a refrigerator overnight. 200 ml of water are then added and the solution is extracted twice with ether. The aqueous phase is lyophilised and the resulting isomer mixture (12 g. 69% of theory) is chromatographed, in portions of 1 g each, from isopropanol/water on 2 pre-packed columns (silica gel 60, size C, (Merck, Darmstadt)) connected in series. On subsequent recrystallisation from ethanol/water, the two diastereomers are obtained in the pure form.

H—Phe—Trp—OH Melting point: 263°–265° C.
$(a)_D^{20} = 14.0°$ (C=0.5; N HCl) after drying at 50° C. and
$(a)_D^{20} = +16.6°$ (c=0.5; N HCl) after drying at 125° C. for 12 hours
H—D—Phe—Trp—OH Melting point: 155° C.
$(a)_D^{20} = -30.6°$ (c=1; methanol).

EXAMPLE 3 (H—D—Phe—D—Trp—OH)

(a) Boc—D—Phe—D—Trp—OMe

To a suspension of 72.8 g (0.286 mol) of H—D—Trp—OMe—HCl in 300 ml of methylene chloride there are added, at 0° C., 32.9 g (0.286 mol) if N-ethylmorpholine and then 75.9 g/0.286 mol) of Boc—D—Phe—OH, dissolved in 300 ml of methylene chloride, and 59 g (0.286 mol) of dicyclohexyl-carbodiimide and the mixture is stirred at 0° C. for 2 hours. The reaction solution is then filtered, 1 l of ethyl acetate is added to the filtrate and the resulting solution is washed with saturated KHCO₃ solution, 10% citric acid solution and saturated NaCl solution. After drying over Na₂SO₄ and evaporating the solution, the dry residue is extracted by stirring with petroleum ether. 112.5 g (84.6% of theory) of Boc—D—Phe—D—Trp—OMe are obtained.

Melting point: 164° C.
$(a)_D^{20} = -11.1°$ (C=0.5; dimethylformamide).

(b) Boc—D—Phe—D—Trp—OH 97.8 g (0.21 mol) of Boc—D—Phe—D—Trp—OMe are saponified with 2 N NaOH as described several times above and the mixture is likewise worked up. 97.6 g of crude Boc—D—Phe—D—Trp—OH which tenaciously holds about 0.5 mol of ethyl acetate, are isolated. A sample is recrystallised from isopropanol/petroleum ether.

Melting point: 128°–130° C.
$(a)_D^{20} = 2.9°$ (c=0.5; methanol).

(c) H—D—Phe—D—Trp—OH 58.6 g (0.13 mol) of Boc—D—Phe—D—Trp—OH are introduced into 200 ml of a saturated solution of HCl in glacial acetic acid and the mixture is kept at room temperature under N₂ for 1 hour. After adding 400 ml of water to the reaction mixture and extracting the mixture with ether and methylene chloride, the organic phases are combined and washed with water. The combined aqueous phases are lyophilised and the product is then dissolved in 200 ml of hot methanol, the solution is filtered and the filtrate is diluted with 200 ml of water and adjusted to pH 5 with concentrated NH₄OH solution. The crystals which separate out are filtered off and washed with methanol/water (1:2).

Yield: 33.4 g (73.2% of theory); melting point: 281°–281° C.
$(a)_D^{20} = 15.5°$ (c=0.5; N HCl)

EXAMPLE 4 H—D—Phe—D—Trp—OMe.HCl 10.6 g (22.8 mmols) of Boc—D—Phe—D—Trp—OMe are dissolved in 50 ccs of glacial acetic acid (saturated with HCl) and the solution is kept at room temperature under nitrogen for 1 hour. After adding 100 ccs of water, the mixture is extracted by shaking twice with methylene chloride, the organic phases are washed with water, the combined aqueous phases are lyophilised and the dry residue is crystallised from 150 ccs of ethanol by adding 150 ccs of petroleum ether.

(a) $D^{20} = -0.8°$ (c=0.5, methanol)
Yield: 7.4 g (81.3% of theory), melting point: 145° C.

EXAMPLE 5 Ac—D—Phe—D—Trp—OMe

To a suspension of 5.6 g (13.9 mmols) of H—D—Phe—Trp—OMe, HCl in 400 ccs of methylene chloride there are added, at 0° C., first 2 ml of triethylamine and then 1.64 ml of thioacetic acid and the mixture is warmed to room temperature. After stirring for 4 hours, it is cooled again to 0° C. and a further 1.64 ccs of thioacetic acid are added since starting material is still present. The reaction mixture is kept in a refrigerator overnight, is filtered and the filtrate is diluted with methylene chloride and extracted with N NaHCO₃, N HCl and water. After drying the organic phase over Na₂SO₄, it is evaporated to dryness in vacuo, the residue is extracted by stirring with diisopropyl ether and the product is then recrystallised from toluene/petroleum ether.

Yield: 5.45 g (95.5% of theory), melting point: 139°–140° C.
$(a)_D^{20} = -7.2°$ (C=0.5, methanol).

EXAMPLE 6 Ac—D—Phe—D—Trp—OH 7.3 ml of N NaOH are added dropwise to a solution of 2.7 g (6.6 mmols) of Ac—D—Phe—D—Trp—OMe in 15 ml of tetrahydrofurane and 1.5 ml of water at °C., whilst stirring, and the mixture is kept at 0° C. for 1 hour. It is diluted with 80 ml of water, neutral substances are extracted with ethyl acetate and the aqueous phase is acidified with concentrated citric acid solution and extracted again with ethyl acetate. The organic phase is dried over Na₂SO₄ and evaporated to dryness in vacuo and the dry residue is crystallised from ethanol/petroleum ether (1:1).

Yield: 2.15 g (82.5% of theory), melting point: 228°–229° C.
$(a)_D^{20} = -11.8°$ (c=0.5; dimethylformamide).

EXAMPLE 7 Ac—D—Phe—D—Trp—NH₄

A solution of 2.7 g (6.6 mmols) of Ac—D—Phe—D—Trp—OMe of 30 ml of methanol and 3 ml of tetrahydrofurane is saturated with ammonia gas at 0° C., then kept at room temperature for 2 days and subsequently evaporated to dryness in vacuo. The residue is extracted by stirring with ether, the product is suspended in hot ethanol, petroleum either is added to the warm suspension and the precipitate is filtered off.

Yield: 2.15 g (82.5% of theory), melting point: 239°–241° C.
$(a)_D^{20} = +20.6°$ (c=0.5; dimethylformamide)
calculated: C 67.33% H 6.1% N 14.28%; found: C 67.10% H 6.07% N 14.24%.

EXAMPLE 8 (H—D—Phe—Trp—NH₂)

(a) Boc—D—Phe—D—Trp—NH₂

Ammonia gas (dried over soda lime) is passed into a suspension of 46.6 g (0.1 mol) of Boc—D—Phe—D—Trp—OMe in 600 ml of methanol and 60 ml of tetrahydrofurane at 0° C., whilst stirring, until the suspension is saturated. After leaving to stand overnight, the solution is filtered and the filtrate is evaporated. The residue is dissolved in 150 ml of acetone under the influence of heat and 150 ml of petroleum are then added. The solid which crystallises out as a result of cooling and triturating is filtered off.

Yield: 39.6 (88% of theory), melting point: 176°–178° C.

$(a)_D^{20} = +14.6°$ (c=0.5; dimethylformamide).

(b) H—D—Phe—D—Trp—NH₂

150 ml of glacial acetic acid (saturated with HCl) are added to 39.5 g (87.6 mmols) of Boc—D—Phe—D—Trp—NH₂ and the solution formed is left to stand at room temperature for 1 hour. About 400 ml of water are added to the batch, which is extracted by shaking twice with methylene chloride. The methylene chloride solution is washed once with water. The combined aqueous phases are concentrated and the residual solution is brought to pH 7 to 8 by adding concentrated ammonia solution. The solid which crystallises out as a result of trituration is filtered off and washed with water. The product is suspended in 300 ml of warm ethanol, 300 ml of petroleum ether are added and, after cooling, the product is filtered off.

Yield: 22.5 g (73.3% of theory), melting point: 183° C.

$(a)_D^{20} = +15.6°$ (c=0.5, dimethylformamide).

Among the new dipeptide salts of the invention, those salts that are pharmaceutically acceptable are particularly important and are preferred. These salts include the acid addition salt of inorganic or organic acids (e.g. hydrochloric, sulphuric, acetic, propionic, etc.) or alkali or alkaline earth metal bases.

The new free dipeptides of the general formula I and their salts can be interconverted in any suitable manner; methods for such interconversion are known in the art.

The present invention also comprises pharmaceutically acceptable bioprecursors of the active compounds of the present invention.

For the purpose of this specification the term 'pharmaceutically acceptable bioprecursor' of an active compound of the invention means a compound having a structural formula different from the active compound but which nonetheless, upon administration to an animal is converted in the patient's body to the active compound.

What is claimed is:

1. A method of treating tissues in a warm-blooded animal which comprises administering to said animal a histolytically effective amount of a compound which is a dipeptide of the formula R—Phe—Trp—R₁     (I)

an acid addition salt or a base addition salt thereof or a stereoisomer thereof, in which Phe denotes the radical

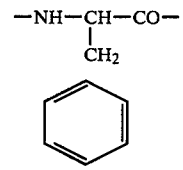

Trp denotes the radical

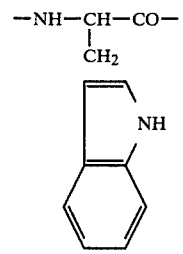

R denotes a hydrogen atom or a C₁ to C₆ alkanoyl group optionally substituted by a hydroxyl group or one or more halogen atoms and R₁ denotes a hydroxyl, C₁ to C₄ alkoxy, amino, C₁ to C₄ alkylamino or di-C₁ to C₄ alkylamino group either alone or in admixture with a diluent or in the form of a medicament.

2. A method according to claim 1 in which the active compound is administered in an amount of 1 to 50 mg per kg body weight per day.

3. A method according to claim 1 or 2, in which the active compound is administered locally.

* * * * *

UNITED STATES PATENT AND TRADEMARK OFFICE
CERTIFICATE OF CORRECTION

PATENT NO. : 4,349,543
DATED : September 14, 1982
INVENTOR(S) : Haireddin Jacobi, et al It is certified that error appears in the above—identified patent and that said Letters Patent is hereby corrected as shown below:

Col. 3, line 3    Insert omitted word --intracutaneous-- after "subcutaneous or"

Signed and Sealed this

Tenth Day of May 1983

[SEAL]

Attest:

GERALD J. MOSSINGHOFF

Attesting Officer    Commissioner of Patents and Trademarks